(12) United States Patent
Song et al.

(10) Patent No.: US 9,777,296 B2
(45) Date of Patent: Oct. 3, 2017

(54) METHOD FOR PRODUCING BIOPRODUCTS USING HYDROLYZED ORGANIC WASTES OF FERMENTATION

(71) Applicants: GS CALTEX CORPORATION, Seoul (KR); CHANGHAE ETHANOL CO., LTD., Jeonju-si, Jeollabuk-do (KR)

(72) Inventors: Hyo-Hak Song, Daejeon (KR); Julia Lee, Yongin-si (KR); Gi-Wook Choi, Jeonju-si (KR); Se-Kwon Moon, Jeonju-si (KR)

(73) Assignees: GS CALTEX CORPORATION, Seoul (KR); CHANGHAE ETHANOL CO., LTD., Jeonju-si, Jeollabuk-do (KR)

(*) Notice: Subject to any disclaimer, the term of this patent is extended or adjusted under 35 U.S.C. 154(b) by 215 days.

(21) Appl. No.: 14/400,685

(22) PCT Filed: May 14, 2013

(86) PCT No.: PCT/KR2013/004256
§ 371 (c)(1),
(2) Date: Nov. 12, 2014

(87) PCT Pub. No.: WO2013/172628
PCT Pub. Date: Nov. 21, 2013

(65) Prior Publication Data
US 2015/0140627 A1    May 21, 2015

(30) Foreign Application Priority Data
May 14, 2012   (KR) .................. 10-2012-0051083

(51) Int. Cl.
*C12P 7/06* (2006.01)
*C12P 7/08* (2006.01)
(Continued)

(52) U.S. Cl.
CPC .................. *C12P 7/06* (2013.01); *C12N 1/16* (2013.01); *C12N 1/20* (2013.01); *C12P 7/08* (2013.01);
(Continued)

(58) Field of Classification Search
CPC ...... C12P 7/06; C12P 7/18; C12P 7/56; C12P 7/40; C12P 7/08; C12N 1/20; C12N 1/16
See application file for complete search history.

(56) References Cited

U.S. PATENT DOCUMENTS 8,685,684 B2 *   4/2014   Lee .................. C12P 5/023
                                                  435/163
2002/0164731 A1   11/2002  Eroma et al.
(Continued)

FOREIGN PATENT DOCUMENTS

KR   20110029065 A       3/2011
KR   WO 2011/031104  *   3/2011
(Continued)

OTHER PUBLICATIONS

Nick Huige (Brewery By-Products and Effluents, (2006) Taylor & Francis Group, LLP, pp. 655-713).*
(Continued)

*Primary Examiner* — Alexander Kim
(74) *Attorney, Agent, or Firm* — Hauptman Ham, LLP

(57) ABSTRACT

Provided is a method for producing bioproducts, including the steps of: culturing a first microorganism to produce bioalcohol; hydrolyzing the first microorganism; separating the bioalcohol; obtaining wastes from the hydrolyzed bioalcohol fermentation; and inoculating a second microorganism into the wastes from the hydrolyzed bioalcohol fermentation.

13 Claims, 8 Drawing Sheets

| (51) | Int. Cl. | |
|---|---|---|
| | *C12P 7/40* | (2006.01) |
| | *C12N 1/16* | (2006.01) |
| | *C12N 1/20* | (2006.01) |
| | *C12P 7/18* | (2006.01) |
| | *C12P 7/56* | (2006.01) |

(52) U.S. Cl.
 CPC ....... *C12P 7/18* (2013.01); *C12P 7/40* (2013.01); *C12P 7/56* (2013.01); *Y02E 50/17* (2013.01)

(56) References Cited

U.S. PATENT DOCUMENTS

| 2007/0031919 A1 | 2/2007 | Dunson, Jr. et al. |
| 2008/0003654 A1 | 1/2008 | Hirl |
| 2012/0231511 A1* | 9/2012 | Lee .................. C12P 5/023 435/113 |

FOREIGN PATENT DOCUMENTS

| WO | 2009043012 A1 | 4/2009 |
| WO | 2009108908 A1 | 9/2009 |
| WO | 2011006019 A2 | 1/2011 |
| WO | 2011056991 A1 | 5/2011 |

OTHER PUBLICATIONS

European Search Report dated May 27, 2015 in connection with the counterpart European Patent Application No. 13790236.7, citing the above references.

Amartey Sam A. et al., Corn Steep Liquor as a Source of Nutrients for Ethanologic Fermentation by Bacillus Stearothermophilus T-13, Scientific Paper, 2000, pp. 65-71, vol. 19, No. 1, Bulletin of the Chemists and Technologists of Macedonia, UK.

Vasimon Ruanglek et al., Evaluation of Thai agro-industrial wastes for bio-ethanol production by Zymomonas mobilis, 2006, pp. 1432-1437, vol. 41, Elsevier.

M.M. Silveira et al., Production of glucose-fructose oxidoreductase and ethanol by Zymomonas mobilis ATTC 29191 in medium containing corn steep liquor as a source of vitamins, 2001, pp. 442-445, vol. 55, Springer-Verlag.

International Search Report for PCT/KR2013/004256 dated Aug. 21, 2013, citing the above reference(s).

* cited by examiner

HYDROLYZED FERMENTED WASTE GROUP
(GLUCOSE ○, LACTIC ACID ●)
NON-HYDROLYZED FERMENTED WASTE GROUP
(GLUCOSE ⊓, LACTIC ACID ■)
CONTROL GROUP (GLUCOSE △, LACTIC ACID ▲)

METHOD FOR PRODUCING BIOPRODUCTS USING HYDROLYZED ORGANIC WASTES OF FERMENTATION

TECHNICAL FIELD

The present invention relates to a method for producing bioproducts using hydrolyzed organic wastes of fermentation.

BACKGROUND ART

In order to product bioproducts through fermentation process using microorganism, various kinds of nutrient components required for growth of microorganism need to be added to medium. The medium is generally classified into synthetic medium containing only components which are clearly defined in chemistry such as inorganic salts, amino acids, vitamins, and the like, and complex medium containing all components required for the growth of microorganism such as peptone, corn steep liquor, yeast extract, and the like, even though some of the components are not defined yet.

However, in the synthetic medium, there is a problem in that microorganisms which are not capable of being grown even in the synthetic medium containing all nutrient components known so far are present in many numbers. In particular, the cost of amino acids and vitamins to be added to the synthetic medium are significantly expensive, there is limitation in using the expensive materials as a nutrient component of a medium in microorganism fermentation process mass-producing low-cost materials such as biofuels and bioproducts.

Accordingly, effort to develop a complex nutrient source not only containing all nutrient components required for growth of the microorganism and production of desired metabolite through microorganism fermentation but also being cheap in cost has been actively conducted all over the world. As the complex nutrient source, there are peptone, corn steep liquor, yeast extract, and the like, wherein some of them have been used in industrial processes producing various materials required for food industry, such as organic acids, amino acids, nucleic acids, and the like, through microorganism fermentation.

In the case of peptone, the nutrient components required for the growth of the microorganism and the production of the desired metabolite through microorganism fermentation are present in an excessive amount; however, the cost thereof is relatively expensive to produce biofuels and bioproducts through microorganism fermentation.

In addition, corn steep liquor (CSL) has an advantage in that the cost is cheap; however, sulfuric acid is used in processing and immersing processes of corn, such that the sulfuric acid as contained in the corn steep liquor. The sulfuric acid may inhibit the growth of the microorganism and the production of the desired metabolite through microorganism fermentation. In addition, as compared to the peptone or yeast extract, the corn steep liquor has relatively insufficient nutrient components which are capable being utilized by the microorganism, such that a relative large amount of corn steep liquor needs to be added as compared to an amount of the peptone or the yeast extract. In fact, in the case of using the medium containing the corn steep liquor as the nutrient component for the growth of the microorganism and the production of the desired metabolite through microorganism fermentation, it has reported that a rate of the growth of the microorganism and productivity of the desired metabolite are decreased (Amartey et al., Bullet. Chem. Technol., Macedonia, 19:65, 2000 Silveira et al., Appl. Microbiol. Biotechnol., 55:442, 2001).

Meanwhile, the yeast extract is generally made of *Saccharomyces cerevisiae* which is used in breweries and baking industry, and is useful for enhancing productivity of the desired metabolite as well as promoting the growth of the microorganism. However, the yeast extract is made by extracting the yeast itself, such that the preparation cost is high.

Accordingly, the present inventors studied a method for producing bioproducts at high efficiency and low cost, and as a result, found that in the case of using fermented wastes remaining after biofuels are produced using microorganism fermentation, a large amount of fermented wastes are capable of being recycled as they are, and the bioproducts also have high productivity. In addition, the present inventors found that after the biofuels are produced, microorganism in fermented products is hydrolyzed before separating the biofuels to be obtained, the nutrient components in the fermented wastes remaining after the biofuels are separated are more increased, such that the bioproducts have remarkably high productivity, thereby completing the present invention.

DISCLOSURE

Technical Problem

An object of the present invention is to provide a method for producing bioproducts at high efficiency and low cost.

Technical Solution

In order to achieve the object of the present invention, according to an exemplary embodiment of the present invention, there is provided a method for producing bioproducts using hydrolyzed wastes of fermentation.

Advantageous Effects

According to the production method of the present invention, the bioproducts may be produced at high productivity and low cost.

DESCRIPTION OF DRAWINGS

The above and other objects, features and advantages of the present invention will become apparent from the following description of preferred embodiments given in conjunction with the accompanying drawings, in which.

BEST MODE

Figure 1:
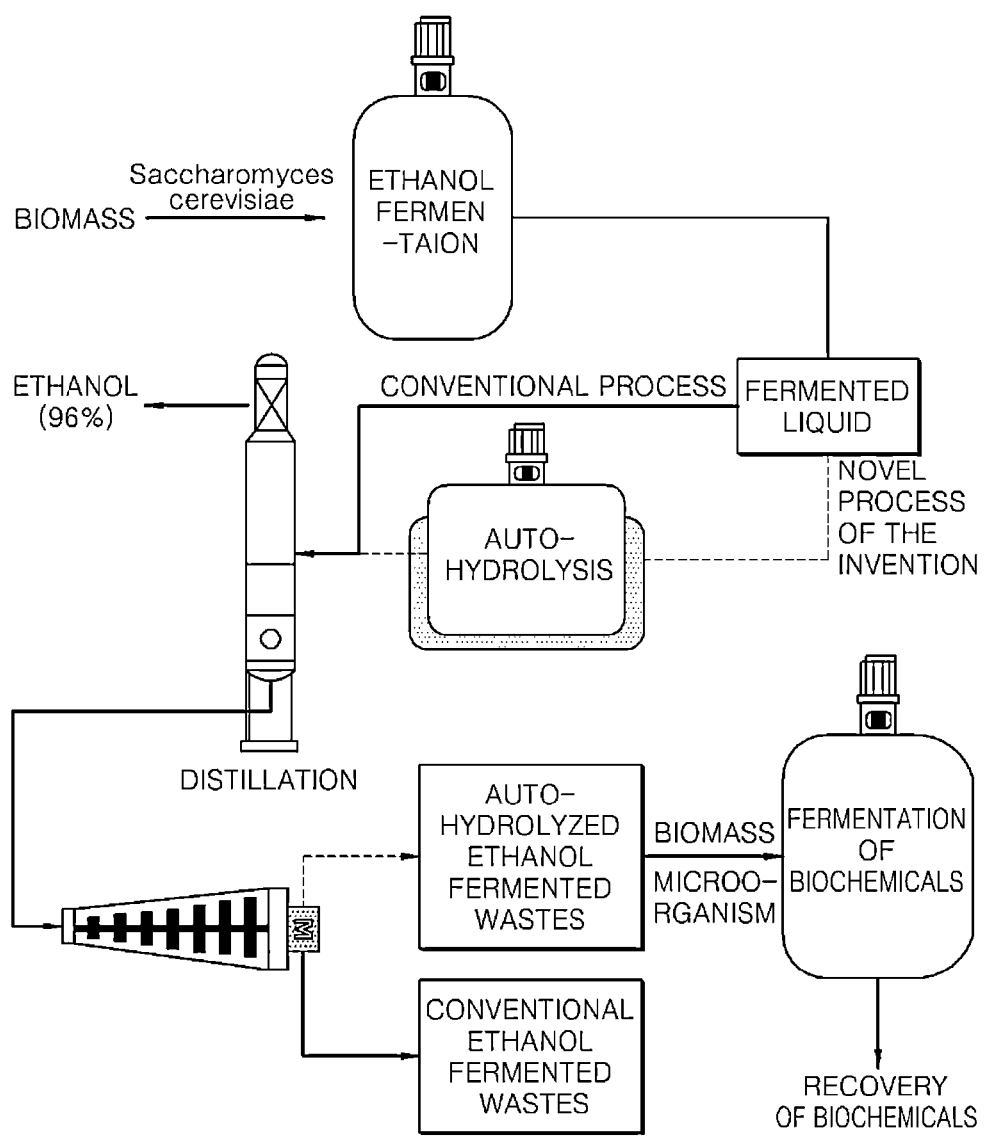
FIG. 1 is a diagram showing comparison between a method for producing bioproducts using hydrolyzed fermented wastes of the present invention and a method for producing bioproducts without performing a hydrolysis process.

The present invention provides a method for producing bioproducts including:
  culturing a first microorganism to produce bioalcohol;
  hydrolyzing the first microorganism;
  separating the bioalcohol;
  obtaining fermented wastes; and
  inoculating a second microorganism into the fermented wastes (FIG. 1).

Hereinafter, the present invention will be described in detail.

First Microorganism

The first microorganism of the present invention is a microorganism producing bioalcohol from biomass. The first microorganism of the present invention may be a wild type, mutant, or recombinant microorganism. The first microorganism is the same as or different from the second microorganism. The first microorganism of the present invention is not limited in view of kind as long as it is capable of producing bioalcohol from biomass, but yeast, that is, *Saccharomyces cerevisiae* is preferably used. In addition, as the first microorganism, two or more kinds of microorganisms may be simultaneously or sequentially used.

Biomass

The first microorganism of the present invention produces bioalcohol using carbon source, wherein the carbon source is preferably biomass. The biomass is not specifically limited as long as it is general biomass used in producing bioalcohol For example, the biomass of the present invention may be wood, corn, tapioca, sugar cane, glycerol, and the like, but is not limited thereto. A person skilled in the art may select appropriate biomass depending on supply and demand conditions of the biomass, kinds of the first microorganism, and the like.

Bioalcohol

The bioalcohol of the present invention is produced by culturing the first microorganism from the biomass. For example, the bioalcohol of the present invention may be ethanol, propanol, propanediol, dihydroxy acetone phosphate, butanol, butanediol, and the like, preferably, may be ethanol.

Culturing of First Microorganism

A culturing method of the first microorganism is not specifically limited as long as the first microorganism is appropriately cultured for producing bioalcohol. For example, the first microorganism may be fermentation-cultured by batch, continuous, or fed-batch process, and a person skilled in the art may appropriately select culture conditions, and the like, of the first microorganism, depending on kinds of the first microorganism, kinds of the bioalcohol to be produced, kinds of carbon source, and the like.

Hydrolysis

Hydrolysis of the first microorganism is to hydrolyze the first microorganism, which is referred to as autolysis, to release nutrient components such as proteins, amino acids, and the like, in the microorganism into an aqueous solution, that is, on a medium. In particular, the first microorganism is hydrolyzed, such that proteins in the microorganism, and the like, are decomposed into amino acids to increase a content of amino acids in fermented wastes, wherein these amino acids are used as important nutrient components for growth of the second microorganism and production of the bioproducts in post processes.

The hydrolysis may be performed by adding hydrolase into the medium, or by auto-hydrolyzing the first microorganism. However, as compared to the addition of the hydrolase, the auto-hydrolysis of the first microorganism is more advantages in that cost is low and the process itself is simple.

Auto-Hydrolysis

As described above, the hydrolysis of the first microorganism of the present invention is preferably auto-hydrolysis. The auto-hydrolysis is preferably performed in a culture medium containing the first microorganism under conditions of 40 to 65° C. and pH 4.5 to 7.0. More preferably, the auto-hydrolysis of the present invention is performed under conditions of 40 to 50° C. and pH 5.0 to 6.5, and further preferably, the auto-hydrolysis of the present invention is performed under conditions of 42.5 to 47.5° C. and pH 5.25 to 6.25. The auto-hydrolysis may be performed for 1 to 42 hours, preferably, for 1 to 24 hours, more preferably, 6 to 18 hours, and further preferably, 8 to 16 hours. Under the above-described conditions of temperature and pH, the first microorganism produces enzymes for auto-hydrolysis, and the auto-hydrolysis of the first microorganism, that is, autolysis, occurs by the enzymes. Accordingly, most of proteins in the first microorganism are decomposed into amino acids and released into an aqueous solution, that is, the medium.

The auto-hydrolysis is preferably performed after the bioalcohol is produced by culturing the first microorganism, but before the produced bioalcohol is separated and recovered. In general, the bioalcohol is separated and recovered by distillation. At this moment, the enzymes of first microorganism are inactivated by high temperature in the distillation process before proteins are decomposed into amino acids capable of directly being used as nutrient components. That is, after the bioalcohol is separated and recovered by the distillation, even though temperature and pH of the fermented wastes are adjusted, the enzymes of first microorganism are already inactivated, such that the auto-hydrolysis does not occur.

Separation of Bioalcohol

The bioalcohol is separated by methods generally performed in the art, and a method for separating bioalcohol is not specifically limited. However, separating and recovering the bioalcohol are preferably performed by distillation in view of cost and efficiency. For example, when the auto-hydrolyzed ethanol fermented wastes are transferred into a distillation column, and distilled by increasing a temperature to 80~90° C., ethanol having 95% or more purity may be recovered.

Fermented Wastes

The fermented wastes of the present invention are fermented wastes remaining after separating and recovering the bioalcohol. The fermented wastes are already in a hydrolyzed state, and contain the dead first microorganism, proteins, amino acids, and proteins or amino acids released from the first microorganism, the nutrient components, and the like. Accordingly, the fermented wastes of the present invention contain the nutrient components required for the growth of the second microorganism and the production of the bioproducts in abundance as compared to non-hydrolyzed fermented wastes.

Second Microorganism

The second microorganism of the present invention is not specifically limited as long as it is capable of producing the bioproducts of the present invention. The second microorganism of the present invention may be a wild type, mutant, or recombinant microorganism. In addition, the second microorganism of the present invention may be obtained by simultaneously or sequentially culturing two or more kinds of microorganisms. In addition, the second microorganism of the present invention may be the same as or different from the first microorganism.

For example, the second microorganism of the present invention may be yeast, *Clostridium, E. coli, Bacillus, Anaeromyxobacter, Alcaligenes, Bacteroides, Escherichia, Lactobacillus, Lactococcus, Pichia, Pseudomonas, Ralstonia, Rhodococcus, Saccharomyces, Streptomyces, Thermus, Thermotoga, Thermoanaerobacter, Klebsiella, Streptomycetaceae, Actinomycetaceae, Colinebacterium, Zymomonas*, and the like, but is not limited thereto. A person skilled in the art may select appropriate second microorganism depending on kinds of the desired bioproduct.

A culturing method of the second microorganism is not specifically limited as long as the second microorganism is appropriately cultured for producing bioproducts as the same as that of the first microorganism. For example, the second microorganism may be cultured by batch, continuous, or fed-batch process, and a person skilled in the art may appropriately select culture conditions, and the like, of the second microorganism, depending on kinds of the second microorganism, kinds of the bioproducts to be produced, kinds of carbon source, and the like.

Additives

Water, glucose, maltose, sugar, starch, glycerol, nitrate, ammonium, amino acids, urea, peptides, proteins, carbon sources, and the like, may be added at the time of the culturing the second microorganism. Here, it is obvious that kinds of the additives and amounts thereof are appropriately determined by a person skilled in the art in consideration of kinds of bioproducts to be produced, kinds of the second microorganisms, culture conditions, and the like.

Bioproducts

The bioproducts of the present invention, which are a material usable as a raw material or an additive to be added to the raw material in a preparation process of chemicals, contain alcohols, organic acids, amino acids, enzymes, biodegradable polymers, and the like, which are producible through fermentation of microorganism.

The alcohol may be alcohol having 6 or less carbon atoms and contain one or two or more hydroxyl groups. For example, the alcohol of the bioproducts of the present invention includes ethanol, propanol, propanediol, dihydroxyacetone phosphate, butanol, butanediol, and the like, wherein the alcohol may be the same as or different from the bioalcohol produced by the first microorganism. However, in consideration of production efficiency, a case in which the alcohol produced by the second microorganism is different from the alcohol produced by the first microorganism is more effective.

The organic acid may be an organic acid having 6 or less carbon atoms and contain one or two or more carboxylic groups. For example, the organic acid of the present invention includes lactic acid, butyric acid, succinic acid, hydroxypropionic acid, and the like.

The amino acid of the present invention is not specifically limited as long as it is an amino acid which is useful in industry. For example, the amino acid of the present invention includes lysine, methionine, threonine, and the like.

Biodegradable polymer of the present invention is a polymer useful in industry, and for example, biopolyester, but the present invention is not limited thereto.

Separation of Bioproducts

The method for producing the bioproducts of the present invention may further include culturing the second microorganism to produce bioproducts; and separating and purifying the bioproducts.

[Exemplary Embodiments]

Advantages and features of the present invention and methods to achieve them will be elucidated from exemplary embodiments described below in detail with reference to the accompanying drawings. However, the present invention is not limited to exemplary embodiment disclosed herein but will be implemented in various forms. The exemplary embodiments are provided by way of example only so that a person of ordinary skilled in the art can fully understand the disclosures of the present invention and the scope of the present invention. Therefore, the present invention will be defined only by the scope of the appended claims.

<Material and Method>

Ethanol Fermented Liquid

An ethanol fermented liquid was directly obtained from a commercial ethanol production plant through microorganism fermentation by ChangHae Ethanol Co. Ltd., producing ethanol in an industrial scale. ChangHae Ethanol Co. Ltd., sells the commercial ethanol obtained by fermenting *Saccharomyces cerevisiae* strain which is an ethanol-producing strain to produce about 90 g/L of ethanol from biomass such as sugar cane, tapioca, and the like, and then primarily distilling the fermented liquid at 80 to 90° C. to provide final purity of 95% or more. Before the distillation of the ethanol in the method for producing ethanol through the microorganism fermentation, the ethanol fermented liquid was obtained and the following experiments were performed.

Yeast Extract

The commercially available product (Difco Labs., Detroit, USA) was purchased and used as yeast extract.

Non-Hydrolyzed Wastes of Fermentation

The ethanol fermented liquid was subjected to direct distillation process without performing the hydrolysis process to separate and recover ethanol. In addition, the remaining ethanol fermented wastes were represented by "non-hydrolyzed wastes of fermentation", and used for the following Experimental Examples 2 and 3.

Hydrolyzed Wastes of Fermentation

The ethanol fermented liquid was auto-hydrolyzed under conditions of 45° C. and pH 6.0 for 12 hours. The auto-hydrolyzed ethanol fermented liquid was distilled to separate and recover ethanol, and the remaining wastes were represented by "hydrolyzed wastes of fermentation", and used for the following Experimental Examples 2 and 3.

Analysis of Nutrient Components

As indicators representing nutrient components present in the ethanol fermented wastes and yeast extracts, total-proteins, total-nitrogens, and 16 kinds of amino acids were adopted, and the ethanol fermented wastes were centrifuged at 4° C. and 12,000 rpm for 10 mins, and components of the indicators present in a supernatant liquid were analyzed. Total proteins were analyzed by using bovine serum albumin as a standard material and a protein analysis kit (TP0200, Sigma-Aldrich, Inc., St. Louis, Mo., USA). Total nitrogens were analyzed by using Kjeldahl nitrogen analysis method (Tecator Kjeltec Auto 1030 Analyzer, Foss Tecator AB, Hoganas, Sweden). 16 kinds of amino acids were analyzed by using an amino acid analyzer (Amino acid analyzer, Waters 2690, Waters Inc., Milford, Mass., USA).

EXPERIMENTAL EXAMPLE 1

Auto-hydrolysis was performed by changing pH, temperature, and time in a shaking incubator in order to appreciate optimum conditions of the auto-hydrolysis of the ethanol fermented liquid.

<1-1> Efficiency of Auto-Hydrolysis of Ethanol Fermented Liquid Depending on Temperature Auto-hydrolysis was performed under condition of pH 4.5 for 48 hours, but by changing temperature in a range of 40 to 65° C., followed by distillation process at 85° C. to recover ethanol from the hydrolyzed ethanol fermented liquid. After the ethanol was recovered, nutrient components of the auto-hydrolyzed ethanol fermented wastes were analyzed.

Figure 2:
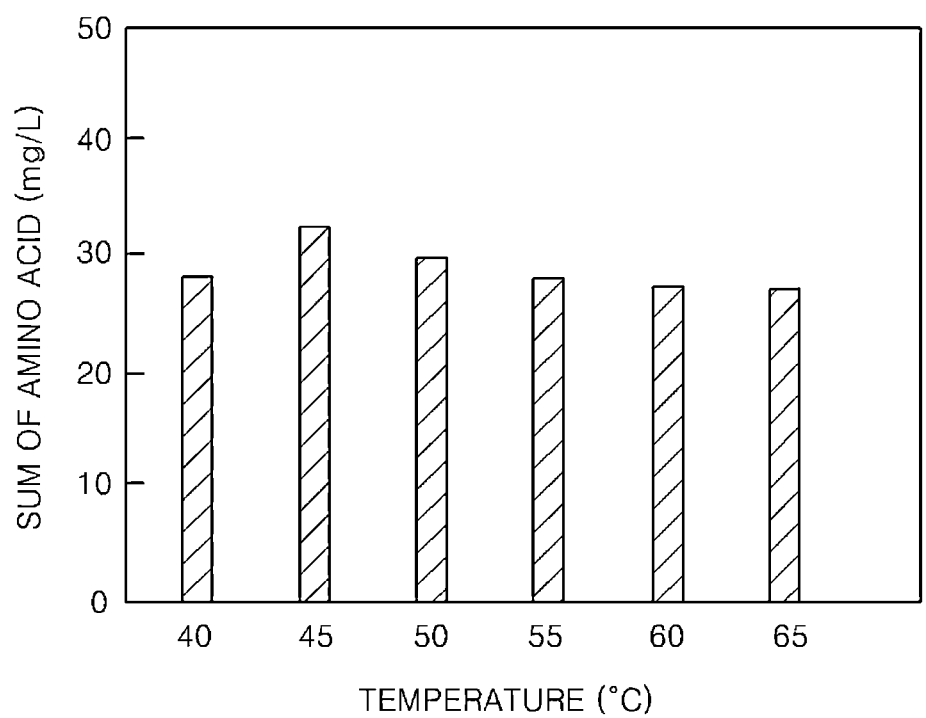
FIG. 2 shows hydrolysis degree of the fermented wastes depending on temperature of hydrolysis.

As a result, it was appreciated that the total proteins, the total nitrogens, and the amino acids with the largest amount were released as an aqueous solution at 40 to 55° C., and in particular, the sum of the total amino acids in the aqueous solution was the highest at 45° C. (FIG. 2).

<1-2> Efficiency of Auto-Hydrolysis of Ethanol Fermented Liquid Depending on pH

Hydrolysis was performed for 48 hours at 45° C. at which the hydrolysis effect was the best in the above <1-1>, but by changing pH from 4.5 to 7.0. Then, the distillation process was performed on the hydrolyzed ethanol fermented liquid at 85° C. to recover ethanol, and after ethanol was recovered, the nutrient components of the auto-hydrolyzed ethanol fermented wastes were analyzed.

Figure 3:
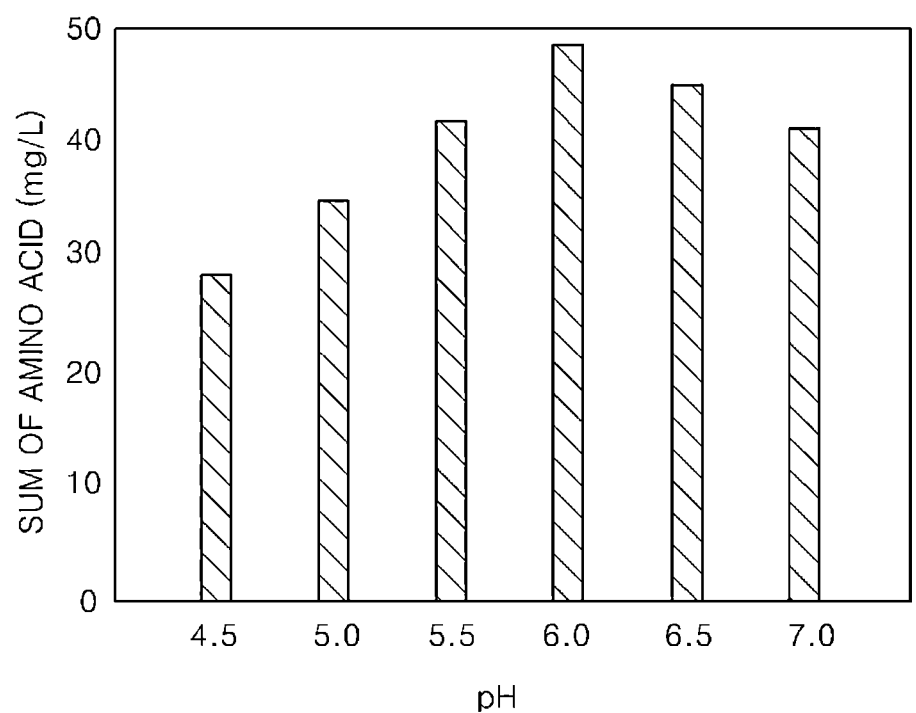
FIG. 3 shows hydrolysis degree of the fermented wastes depending on pH of hydrolysis.

As a result, it was shown that the total proteins, the total nitrogens, and the amino acids with the largest amount were released as an aqueous solution under condition of pH 5.0 to 7.0, and in particular, pH 5.5 to 7.0, and among the results, the sum of the total amino acids in the aqueous solution at the time of auto-hydrolysis at pH 6.0 was the highest (FIG. 3).

<1-3> Efficiency of Auto-Hydrolysis of Ethanol Fermented Liquid Depending on Time Efficiency of auto-hydrolysis was evaluated depending on hydrolysis time under conditions of pH 6.0 and 45° C. at which the auto-hydrolysis efficiency was the highest in the above <1-1> and <1-2>. The auto-hydrolysis was performed under conditions of pH 6.0 and 45° C. from 6 to 42 hours every six hours as a unit, followed by distillation process at 85° C. to recover ethanol from the hydrolyzed ethanol fermented liquid. After the ethanol was recovered, the nutrient components of the auto-hydrolyzed ethanol fermented wastes were analyzed.

Figure 4:
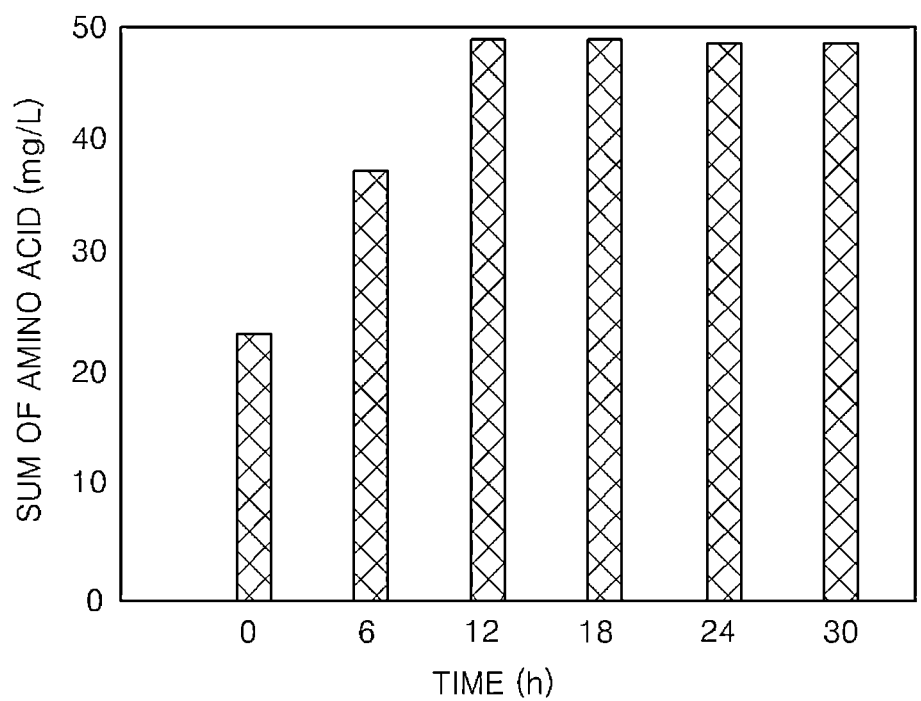
FIG. 4 shows hydrolysis degree of the fermented wastes depending on time of hydrolysis.

As a result, a degree of the auto-hydrolysis of the ethanol fermented liquid was straightly increased up to 12 hours, but afterwards, the auto-hydrolysis did not proceeded any further. Therefore, it was determined that the auto-hydrolysis of the ethanol fermented liquid was preferably performed for 12 hours or more, and in particular, 12 hours is the most efficient condition (FIG. 4).

When summarizing the above <1-1> to <1-3>, the auto-hydrolysis of the ethanol fermented liquid was preferably performed under conditions of 40 to 55° C. and pH 5.0 to 7.0 for 12 hours or more, and in particular, under conditions of 45° C. and pH 6.0, for 12 hours.

EXPERIMENTAL EXAMPLE 2

Nutrient components in yeast extract (1 g/L), non-hydrolyzed fermented wastes, and hydrolyzed fermented wastes were analyzed in order to quantitatively evaluate the nutrient components released into the aqueous liquid in the auto-hydrolysis process of the ethanol fermented liquid.

Result 0.356 g/L of the total proteins and 0.119 g/L of the total nitrogens were present in 1 g/L of the yeast extract, and the sum of 16 kinds of amino acids was 27.05 mg/L. 2.906 g/L of the total proteins and 0.471 g/L of the total nitrogens were present in the non-hydrolyzed fermented wastes, which were 8.2 times higher than that of the yeast extract (1 g/L), and 4.0 times higher than that of the yeast extract (1 g/L), respectively. Meanwhile, the sum of kinds of amino acids in the non-hydrolyzed fermented wastes was 24.11 mg/L, which corresponds to about 90% of that of the yeast extract (1 g/L). Therefore, it was considered that in the growth of the microorganism and the production of the desired metabolite through microorganism fermentation, the non-hydrolyzed fermented wastes are advantageous in view of proteins and nitrogen sources; but the yeast extract (1 g/L) is more advantageous in view of amino acids.

Meanwhile, 3.201 g/L of the total proteins and 0.532 g/L of the total nitrogens were present in the hydrolyzed ethanol fermented wastes. As compared to the existing ethanol fermented wastes, these values of the hydrolyzed fermented wastes were increased by about 10% and 13%, respectively, and as compared to the yeast extract (1 g/L), these values were significantly high corresponding to about 9 times and 4.5 times higher values than those of the yeast extract, respectively. In particular, 48.51 mg/L of the amino acid was present in the hydrolyzed fermented wastes, which was increased by about 100% or more as compared to the non-hydrolyzed fermented wastes. It means that many components usable as the nutrient components for the growth of the microorganism and the production of the desired metabolite through the microorganism fermentation are released into an aqueous solution by the auto-hydrolysis of the ethanol fermented liquid. 48.51 mg/L of the amino acid present in the hydrolyzed fermented wastes was also increased by 80% than 27.05 mg/L of the amino acid present in the yeast extract (1 g/L) (Table 1).

TABLE 1

| Component | Yeast Extract | Non-hydrolyzed Ethanol Fermented Waste | Hydrolyzed Ethanol Fermented Waste |
| --- | --- | --- | --- |
| Total Protein (g/L) | 0.356 | 2.906 | 3.201 |
| Total Nitrogen (g/L) | 0.119 | 0.471 | 0.532 |
| Amino acids (mg/L) | 27.05 | 24.11 | 48.51 |
| Aspartic acid | 1.50 | 0.97 | 1.88 |
| Glutamic acid | 4.99 | 3.55 | 4.64 |
| Serine | 1.58 | 1.38 | 2.37 |
| Glycine | 0.93 | 0.61 | 1.31 |
| Histidine | 0.44 | 0.35 | 0.69 |
| Threonine | 1.50 | 1.17 | 2.58 |
| Arginine | 1.21 | 1.58 | 3.06 |
| Alanine | 2.89 | 2.07 | 4.45 |
| Proline | 0.81 | 4.73 | 9.17 |
| Tyrosine | 0.61 | 1.36 | 3.32 |
| Valine | 1.79 | 1.65 | 2.91 |
| Methionine | 0.85 | 0.34 | 1.46 |
| Isoleucine | 1.75 | 0.65 | 2.22 |
| Leucine | 3.03 | 1.58 | 3.95 |
| Lysine | 1.43 | 1.13 | 2.04 |
| Phenylalnine | 1.74 | 0.99 | 2.46 |

EXPERIMENTAL EXAMPLE 3

Bioproducts Productivity

<3-1> 2,3-Butanediol Productivity

*Klebsiella oxytoca* recombinant strain (*K. oxytoca* ATCC43863 ldhA) culture liquid cultured in a 300 mL flask was inoculated into a 6.6 L bioreactor containing the hydrolyzed fermented wastes or the non-hydrolyzed fermented wastes, respectively, followed by fermentation of batch process to produce 2,3-butanediol. Here, the fermentation conditions were an initial glucose concentration of 300 mM (54 g/L), a fermentation temperature of 37° C. and a stirring rate of 150 rpm, and air was continuously supplied during the culturing at a flow rate of 1 vvm (3 L/min), and pH in the fermentation was adjusted to pH 6.0 using 5N NaOH solution.

The *Klebsiella oxytoca* recombinant strain (*K. oxytoca* ATCC43863 ldhA) is a recombinant strain (*K. oxytoca* ATCC43863 ldhA) obtained by removing ldhA gene encoding a lactic acid biosynthesis-related enzyme (lactate dehydrogenase) from a *Klebsiella oxytoca* wild typed strain (*Klebsiella oxytoca* ATCC43863), and was used as a strain for producing 2,3-butanediol in the present experiment.

Here, a synthetic medium generally used for culturing the *Klebsiella oxytoca* strain was used as a control group, and compositions thereof were shown in the following Table 2. 2,3-butanediol was produced by the same fermentation and culturing method as the fermented wastes except for adding the synthetic medium instead of the hydrolyzed/non-hydrolyzed fermented wastes to the bioreactor.

TABLE 2

| Component | Concentration | Component | Concentration |
|---|---|---|---|
| $K_2HPO_4$ | 8.657 g/L | $FeSO_4 \cdot 7H_2O$ | 0.05 g/L |
| $KH_2PO_4$ | 6.845 g/L | $ZnSO_4 \cdot 7H_2O$ | 0.001 g/L |
| $(NH_4)_2SO_4$ | 6.6 g/L | $MnSO_4 \cdot H_2O$ | 0.001 g/L |
| $MgSO_4 \cdot 7H_2O$ | 0.25 g/L | $CaCl_2 \cdot 2H_2O$ | 0.001 g/L |
| HCl | 10 mL/L | | |

Result

Figure 5:
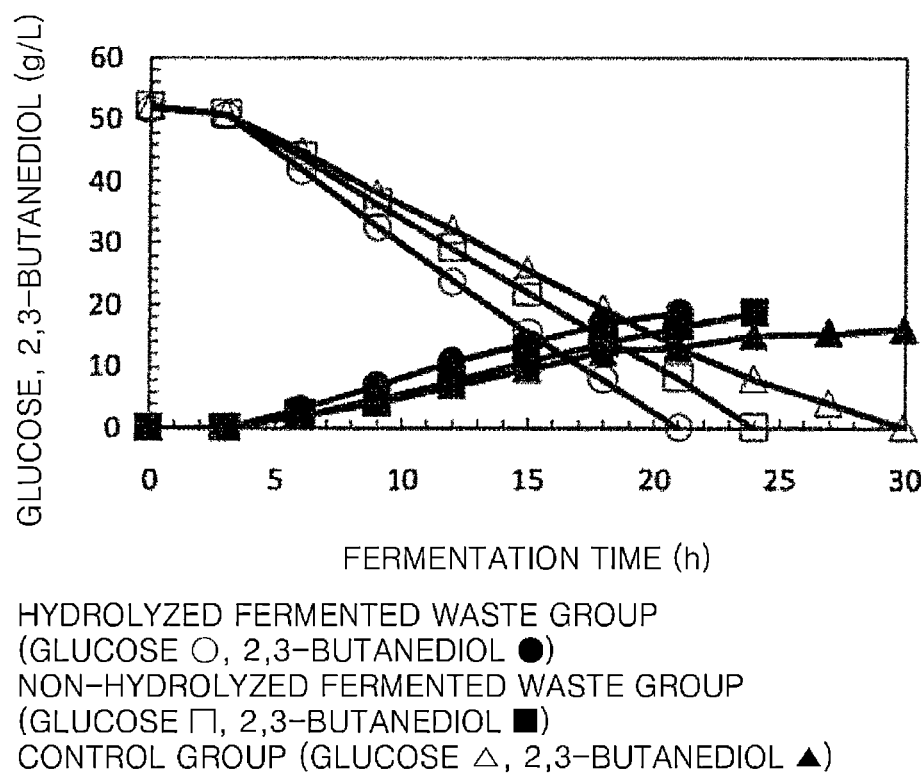
FIG. 5 is a graph showing fermentation profile of glucose consumption and 2,3-butanediol production at the time of using the hydrolyzed fermented wastes or non-hydrolyzed fermented wastes.

In the case of the control group, the *Klebsiella oxytoca* recombinant strain (*K. oxytoca* ATCC43863 ldhA) completely consumed 300 mM glucose added to the medium as a carbon source after fermentation for 30 hours; however, in the case of using the non-hydrolyzed fermented wastes as a medium, the strain completely consumed the same amount of the glucose after fermentation for 24 hours. 2,3-butanediol was produced after 300 mM glucose was completely consumed, wherein in the case of the control group, 16 g/L of 2,3-butanediol was produced, but in the case of using the non-hydrolyzed fermented wastes as a medium, 18 g/L of 2,3-butanediol was produced. Meanwhile, in the case of using the hydrolyzed fermented wastes as a medium, 300 mM glucose was completely consumed after fermentation for 21 hours, and the produced amount of 2,3-butanediol was 18 g/L which is the same as that of the non-hydrolyzed fermented wastes (FIG. 5).

Figure 6:
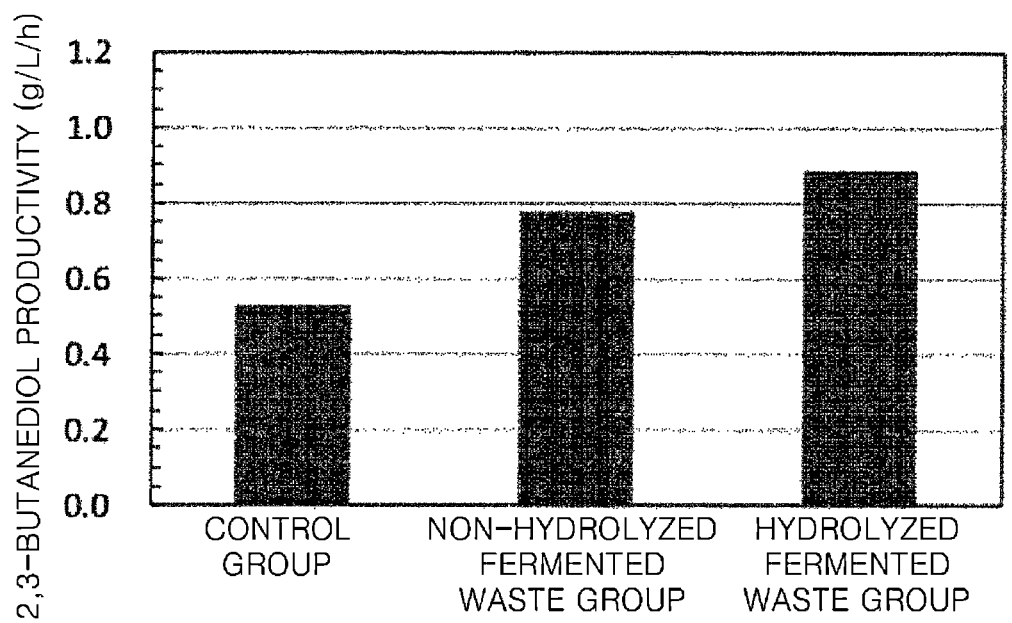
FIG. 6 shows 2,3-butanediol productivity at the time of using the hydrolyzed fermented wastes or the non-hydrolyzed fermented wastes.

In addition, as a result obtained by calculating productivity of 2,3-butanediol, that is, produced amount of 2,3-butanediol per time, it was confirmed that the productivity of 2,3-butanediol of the hydrolyzed fermented wastes was 0.89 g/L/h, which was higher than that of the non-hydrolyzed fermented wastes (0.78 g/L/h) and that of the control group (0.53 g/L/h). It was considered because the nutrient components released into the aqueous solution through the auto-hydrolysis process of the ethanol fermented liquid, and in particular, amino acids, increased the consumption of the glucose and the production rate of 2,3-butanediol, to improve the productivity of 2,3-butanediol (FIG. 6).

<3-2> Lactic Acid Productivity

An experiment for measuring lactic acid productivity was performed by using *Lactobacillus paracasei* strain (*L. paracasei* KCTC 11710BP). Specifically, *Lactobacillus paracasei* strain (*L. paracasei* KCTC 11710BP) culture liquid cultured in 300 mL flask was inoculated into a 6.6 L bioreactor containing the hydrolyzed fermented wastes or the non-hydrolyzed fermented wastes, respectively, followed by fermentation of batch process, wherein fermentation conditions were an initial glucose concentration of 300 mM (54 g/L), a fermentation temperature of 37° C. and a stirring rate of 150 rpm. pH in the fermentation was adjusted to 6.0 by using 10N NaOH solution.

Here, a *Lactobacillus* Growth Medium (LGM) generally used for fermenting the *lactobacillus* was used as a control group, and compositions thereof were shown in the following Table 3. Lactic acid was produced by the same fermentation method as the fermented wastes except for adding the LGM medium instead of the hydrolyzed/non-hydrolyzed fermented wastes to the bioreactor.

TABLE 3

| Component | Concentration |
|---|---|
| Yeast extract | 2 g/L |
| $(NH_4)_2HPO_4$ | 4 g/L |
| Ammonium citrate | 1.5 g/L |
| Sodium acetate | 1.5 g/L |
| $MnSO_4 \cdot 5H_2O$ | 0.012 g/L |

Result

Figure 7:
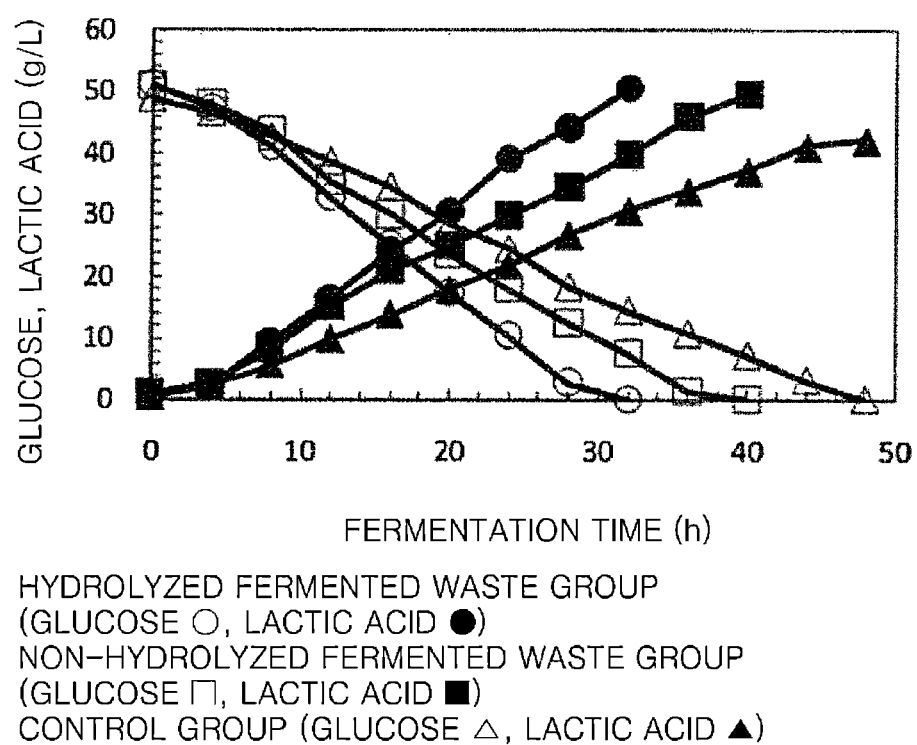
FIG. 7 is a graph showing fermentation profile of glucose consumption and lactic acid production at the time of using the hydrolyzed fermented wastes or the non-hydrolyzed fermented wastes.

In the case of the control group, the *Lactobacillus paracasei* strain (*L. paracasei* KCTC 11710BP) completely consumed 300 mM glucose added to the medium as a carbon source after fermentation for 48 hours; however, in the case of the non-hydrolyzed fermented waste groups, the strain completely consumed the same amount of the glucose after fermentation for 40 hours. The lactic acid was produced after 300 mM glucose was completely consumed, wherein in the case of the control group, 42 g/L of lactic acid was produced, but in the case of the non-hydrolyzed fermented wastes, 49 g/L of lactic acid was produced, which was increased by about 17% as compared to that of the control group. Meanwhile, in the case of using the hydrolyzed fermented wastes as a medium, 300 mM glucose was completely consumed after fermentation for 32 hours, and 50 g/L of lactic acid was produced which is higher than that of the case of using the non-hydrolyzed fermented wastes as a medium (FIG. 7).

Figure 8:
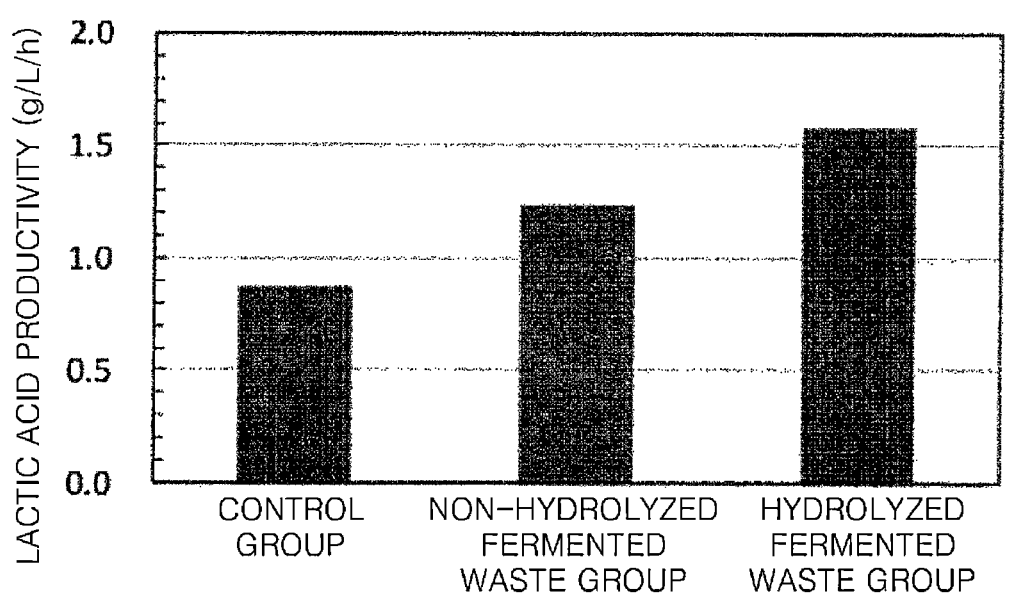
FIG. 8 shows lactic acid productivity at the time of using the hydrolyzed fermented wastes or the non-hydrolyzed fermented wastes.

Meanwhile, in the case of the productivity of lactic acid, that is, produced amount of lactic acid per time, it was confirmed that the productivity of lactic acid of the hydrolyzed fermented wastes was 1.58 g/L/h, which was higher than that of the non-hydrolyzed fermented wastes (1.24 g/L/h) and that of the control group (0.88 g/L/h). It was considered because nutrient components released into the aqueous solution through the auto-hydrolysis process of the ethanol fermented liquid, and in particular, amino acids, increased the consumption of the glucose and the production rate of lactic acid, to improve the productivity of lactic acid (FIG. 8).

INDUSTRIAL APPLICABILITY

According to the method for producing bioproducts of the present invention, the bioproducts may be produced at high efficiency and low cost.

The invention claimed is:

1. A method for producing bioproducts comprising:
    culturing a first microorganism to be fermented and produce a bioalcohol in a culture medium;
    auto-hydrolyzing the first microorganism in the culture medium to produce amino acids, wherein the auto-hydrolyzing occurs by an enzyme of the first microorganism;
    separating the bioalcohol;
    obtaining a fermented waste which is remained after separating the bioalcohol; and
    inoculating a second microorganism into the fermented waste.

2. The method of claim 1, wherein the first microorganism is the same as or different from the second microorganism.

3. The method of claim 1, wherein the bioproduct is the same as or different from the bioalcohol.

4. The method of claim 1, wherein the first microorganism produces the bioalcohol from biomass.

5. The method of claim 1, wherein the auto-hydrolyzing is performed in the culture medium containing the first microorganism under condition of 40 to 65° C.

6. The method of claim 1, wherein the auto-hydrolyzing is performed in the culture medium containing the first microorganism under condition of pH 4.5 to 7.0.

7. The method of claim 1, wherein an amino acid content in the fermented waste obtained after separating the bioalcohol is increased by auto-hydrolyzing.

8. The method of claim 1, wherein the bioalcohol is bioethanol.

9. The method of claim 1, wherein the first microorganism is yeast.

10. The method of claim 1, wherein the second microorganism has productivity of the bioproduct.

11. The method of claim 1, wherein the bioproduct is alcohol or an organic acid.

12. The method of claim 1, wherein the bioproduct is alcohol having 6 or less carbon atoms or an organic acid having 6 or less carbon atoms.

13. The method of claim 1, further comprising:
    culturing the second microorganism to produce the bioproducts; and
    separating and purifying the bioproducts.

* * * * *